US00PP26641P2

(12) United States Plant Patent
Hardy et al.

(10) Patent No.: US PP26,641 P2
(45) Date of Patent: Apr. 19, 2016

(54) ***GAURA* PLANT NAMED 'HARRFOLK'**

(50) Latin Name: *Gaura lindheimeri*
Varietal Denomination: HARRFOLK

(71) Applicants: Rob Hardy, Whitechurch (GB); Rosy Hardy, Whitechurch (GB)

(72) Inventors: Rob Hardy, Whitechurch (GB); Rosy Hardy, Whitechurch (GB)

( * ) Notice: Subject to any disclaimer, the term of this patent is extended or adjusted under 35 U.S.C. 154(b) by 143 days.

(21) Appl. No.: 14/120,851

(22) Filed: Jun. 30, 2014

(51) Int. Cl.
*A01H 5/00* (2006.01)

(52) U.S. Cl.
USPC ..... Plt./432

(58) Field of Classification Search
USPC ..... Plt./432
See application file for complete search history.

*Primary Examiner* — Annette Para
(74) *Attorney, Agent, or Firm* — Penny J. Aguirre

(57) ABSTRACT

A new cultivar of *Gaura lindheimeri*, 'HARRFOLK', that is characterized by its variegated foliage with medium green centers and irregular yellow margins, its flowers that emerge from crimson red buds and have flower petals that are white in color with pink margins (picotee type), and its medium plant height relative to comparative cultivars.

2 Drawing Sheets

Botanical classification: *Gaura lindheimeri.*
Cultivar designation: 'HARRFOLK'.

BACKGROUND OF THE INVENTION

The present invention relates to a new and distinct cultivar of *Gaura* plant, botanically known as *Gaura lindheimeri* 'HARRFOLK' and will be referred to hereafter by its cultivar name, 'HARRFOLK'.

The Inventors discovered the new cultivar, 'HARRFOLK' as a branch mutation of *Gaura lindheimeri* 'HARROSY' (U.S. Pat. No. 22,290) in a container at their nursery in Whitchurch, Hants, United Kingdom in March of 2011.

Asexual propagation of the new cultivar was first accomplished by softwood stem cuttings in Whitchurch, Hants, United Kingdom in June 2011 by one of the Inventors. Asexual propagation by soft stem cuttings has determined that the characteristics of the new cultivar are stable and are reproduced true to type in successive generations.

SUMMARY OF THE INVENTION

The following traits have been repeatedly observed and represent the characteristics of 'HARRFOLK'. These attributes in combination distinguish 'HARRFOLK' as a new and distinct cultivar of *Gaura.*

1. 'HARRFOLK' exhibits variegated foliage with medium green centers and irregular yellow margins.
2. 'HARRFOLK' exhibits large flowers that have petals that are white in color with pink margins (picotee type coloration).
3. 'HARRFOLK' exhibits flower buds that are crimson red in color.
4. 'HARRFOLK' exhibits a medium plant height relative to comparative cultivars.

'HARROSY', the parent plant of 'HARRFOLK', is similar to 'HARRFOLK' in having in having picotee type flowers with petals that are white with pink margins. 'HARROSY' differs from 'HARRFOLK' in having non-variegated foliage and in being about slightly taller in plant height. 'HARRFOLK' can be most closely compared to the cultivars, 'Passionate Rainbow' (U.S. Plant Pat. No. 22,290) and 'Summer Emotions' (U.S. Plant Pat. No. 21,904). 'Passionate Rainbow' is similar to 'HARRFOLK' in having variegated foliage. 'Passionate Rainbow' differs from 'HARRFOLK' in having foliage that is more linear in shape with thinner margins that are whiter in color and in being slightly shorter in plant height. 'Summer Emotions' is similar to 'HARRFOLK' in flower coloration. 'Summer Emotions' differs from 'HARRFOLK' in having foliage that is non-variegated and more linear in shape and in being shorter in plant height.

BRIEF DESCRIPTION OF THE DRAWINGS

The accompanying colored photographs illustrate the overall appearance and distinct characteristics of the new *Gaura*. The photographs were taken of six month-old plants of 'HARRFOLK' as grown in a greenhouse in 9-cm containers in Whitchurch, Hants, United Kingdom.

The photograph in FIG. 1 is a view of a plant of 'HARRFOLK' in bloom.

Figure 1:
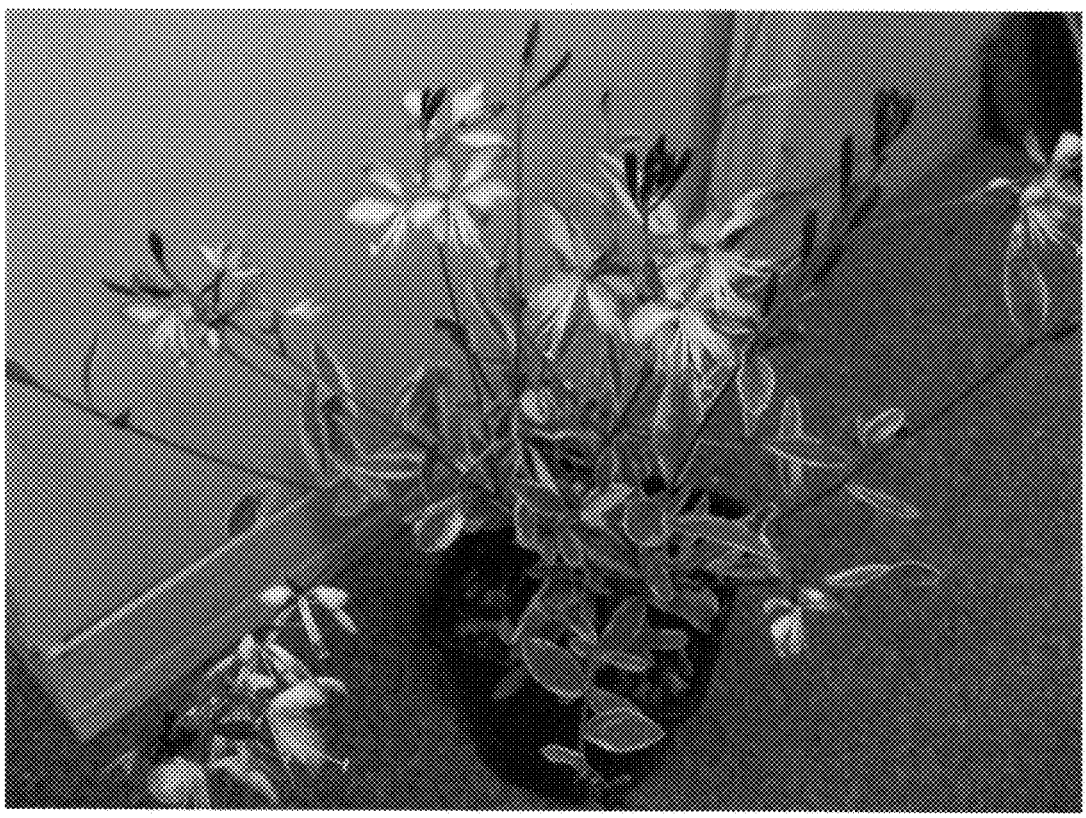
Figure 2:
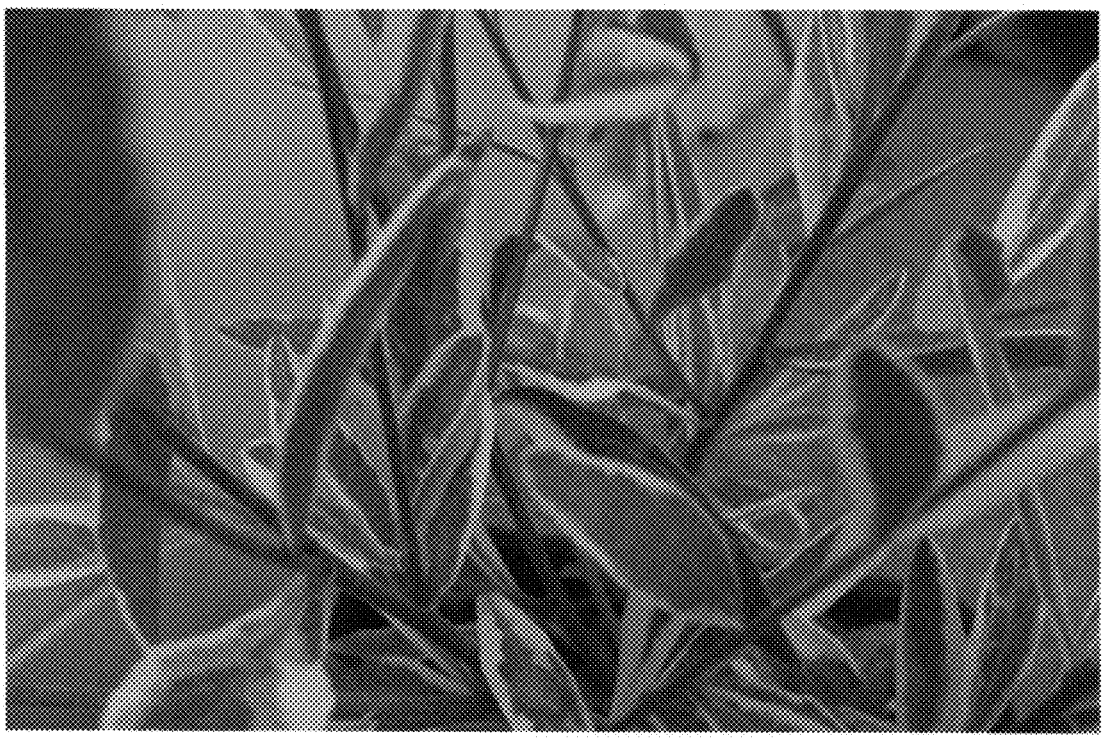

The photograph in FIG. 2 provides a close-up view of the foliage of 'HARRFOLK'.

Figure 3:
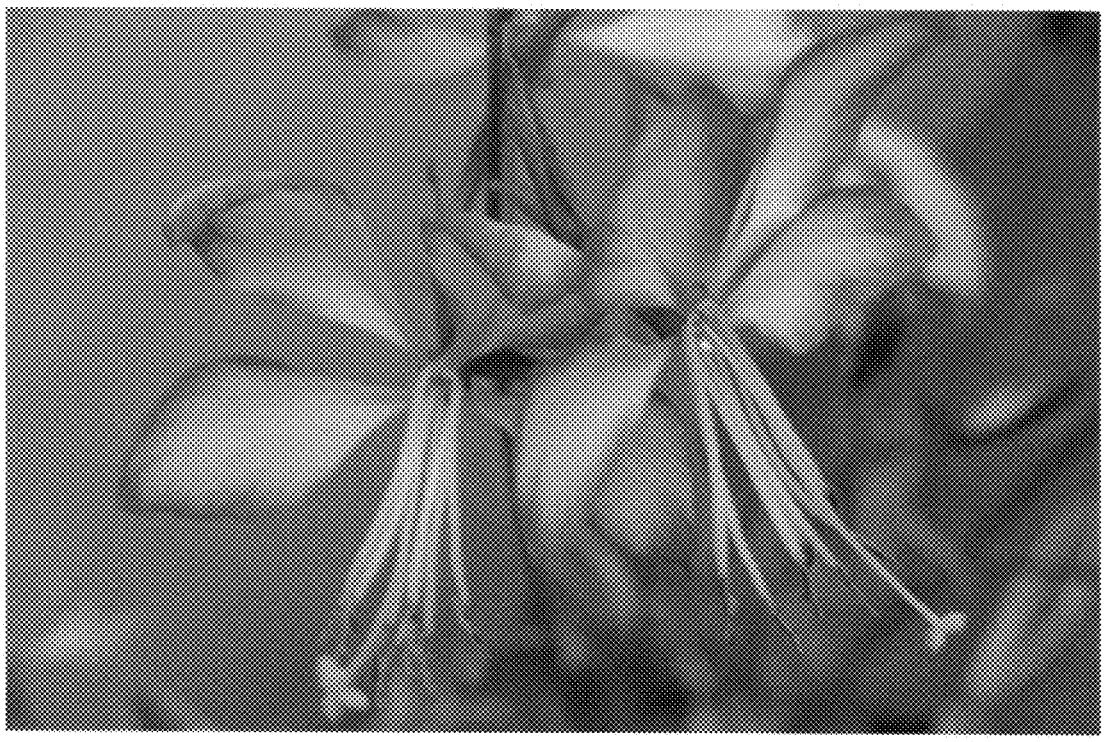

The photograph in FIG. 3 provides a close-up view of the flowers of 'HARRFOLK'.

The colors in the photographs are as close as possible with digital photography techniques available, the color values cited in the detailed botanical description accurately describe the colors of the new *Gaura.*

DETAILED BOTANICAL DESCRIPTION OF THE PLANT

The following is a detailed description of six month-old plants of the new cultivar as grown in a greenhouse in 9-cm containers in Whitchurch, Hants, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—6 weeks in July to September in southern UK.

*Plant habit.*—Herbaceous perennial, semi-upright habit.

*Height and spread.*—Reaches about 76 cm in height and about 50 cm in width.

*Cold hardiness.*—At least in U.S.D.A. zones 5 to 9 (with good winter drainage).

*Diseases and pests.*—No susceptibility or resistance to diseases or pests has been observed.

*Root description.*—Taproot with fibrous secondary roots.

*Branching habit.*—Freely branched, about 30 branches per plant emerging at 45° angles from main stem.

*Growth rate.*—Moderate.

*Propagation.*—Softwood stem cuttings.

Stem description:

*Stem size.*—40 cm in length and 2 mm in diameter, stems are solid.

*Stem shape.*—Round.

*Stem color.*—139C.

*Stem surface.*—Pubescent.

*Internode length.*—Average of 3 cm, ranging between 2 to 5 cm in length.

Foliage description:

*Leaf shape.*—Lanceolate to oblanceolate.

*Leaf division.*—Simple.

*Leaf base.*—Cuneate.

*Leaf apex.*—Obtuse to acute.

*Leaf venation.*—Pinnate, 139D in color on upper and lower surface.

*Leaf margins.*—Entire, occasionally shallowly dentate.

*Leaf attachment.*—Sessile.

*Leaf arrangement.*—Alternate.

*Leaf surface.*—Upper and lower surface pubescent.

*Leaf color.*—Young upper surface; 139C with irregular margins 5D, mature upper surface; develops margins and center areas of 187B, young and mature lower surface; 139C.

*Leaf size.*—Average of 6 cm in length and 1.3 cm in width.

Flower description:

*Inflorescence type.*—Terminal spike.

*Lastingness of flowers.*—About 3 days, self cleaning.

*Inflorescence size.*—About 20 cm in length and 5.2 cm in width.

*Flower type.*—Single.

*Flower size.*—Average of 4.5 cm in height and 2.6 cm in diameter.

*Flower fragrance.*—None.

*Flower number.*—Up to 20 per branch.

*Flower aspect.*—45° to 60° angle from peduncle.

*Flower bud.*—Narrowly ellipsoid with a slightly swollen base, 1.9 cm in length, 3 mm in width, 60C in color.

*Petals.*—4 per flower, lanceolate in shape, rotate, smooth, margins entire, about 2.0 cm in length and 1.1 cm in width, NN155D in color with margins (1 to 5 mm in width) 67B in color with feathering toward the center.

*Sepals.*—4 per flower, linear in shape, strongly reflexed, 1.8 cm in length, 2 mm in width, acute apex, margins entire, involute, surface sparsely pubescent, 185A in color.

*Bract.*—Narrowly elliptic in shape, 7.5 mm in length and 2 mm in width, 138B in center and with margins 150D in color when flowers fully open, 178A in color when flowers in buds.

*Peduncle.*—Round, sparsely pubescent, an average of 20 cm in length and 1 mm in width, 138A in color.

Reproductive organs:

*Gynoecium.*—1 pistil, stigma; 4-lobed, 2 mm in diameter, each lobe 1 mm in length, NN155D in color, style; cylindrical in shape, 2.4 cm in length and 1 mm in width, NN155D in color, ovary; inferior, 4-angled, sparsely pubescent surface, about 5 mm in length and 1 mm in width, N144D in color.

*Androecium.*—8 stamens, anthers; dorsifixed, linear-oblong in shape, 3 mm in length, <1 mm in width, and 175D in color, filament; 1.2 cm in length, <1 mm in width and NN155D in color, pollen; low in abundance and 11C in color.

*Fruit.*—Ovoid woody capsule.

*Seeds.*—3 to 4 seeds per fruit 3 mm in length, 1 mm in width, 176C in color.

It is claimed:

1. A new and distinct cultivar of *Gaura* plant named 'HARRFOLK' as herein illustrated and described.

* * * * *